(12) United States Patent
Kitchen

(10) Patent No.: US 7,029,146 B2
(45) Date of Patent: Apr. 18, 2006

(54) FLAMELESS CANDLE

(75) Inventor: Edward F. Kitchen, P.O. Box 1436, Laguna Beach, CA (US) 92652

(73) Assignee: Edward F. Kitchen, Laguna Beach, CA (US)

( * ) Notice: Subject to any disclaimer, the term of this patent is extended or adjusted under 35 U.S.C. 154(b) by 110 days.

(21) Appl. No.: 10/127,430

(22) Filed: Apr. 22, 2002

(65) Prior Publication Data

US 2003/0198045 A1    Oct. 23, 2003

(51) Int. Cl.
*F21V 3/02* (2006.01)
*F21V 23/00* (2006.01)

(52) U.S. Cl. .................. 362/235; 362/234; 362/392; 362/810

(58) Field of Classification Search ........ 362/184–186, 362/234, 235, 251, 392, 810
See application file for complete search history.

(56) References Cited

U.S. PATENT DOCUMENTS

| | | | | |
|---|---|---|---|---|
| 2,532,800 A | * | 12/1950 | Adinamis et al. ........... 219/473 |
| 2,976,450 A | * | 3/1961 | Benoliel et al. ............ 313/151 |
| 3,749,904 A | * | 7/1973 | Graff ........................... 362/265 |
| 3,761,702 A | * | 9/1973 | Andeweg ..................... 362/161 |
| 4,510,556 A | * | 4/1985 | Johnson ....................... 362/184 |
| 4,866,580 A | * | 9/1989 | Blackerby .................... 362/205 |
| 5,097,180 A | * | 3/1992 | Ignon et al. ............ 315/200 A |
| 5,174,645 A | * | 12/1992 | Chung ......................... 362/392 |
| 5,601,360 A | * | 2/1997 | Paquette ...................... 362/392 |
| 6,066,924 A | * | 5/2000 | Lederer ....................... 362/392 |
| 6,719,443 B1 | * | 4/2004 | Gutstein et al. ............. 362/392 |

* cited by examiner

*Primary Examiner*—Alan Cariaso

(57) ABSTRACT

An electric lighting device created for use as a safe, long lasting, authentic looking alternative to a flame bearing candle. This electric 'candle' being made from real candle wax, or hollowed out candles with the wicks removed. The 'candle' can be scented or colored, and the glow is authentic and pleasing being viewed through real candle wax. Miniature lamps suspended in a clear or yellowish heat resistant medium provide the source lighting. The glow of the artificial flame is color and volume-of-output matched to that of a real flame and realism is added by simulated flame movement with the use of an adjustable oscillator circuit hidden inside the candle. This flameless 'candle' can be used safely unattended, and is realistic in that real candle wax, or real used candles, are used for the body of the device.

1 Claim, 4 Drawing Sheets

FLAMELESS CANDLE

CROSS-REFERENCE TO RELATED APPLICATIONS

N/A

STATEMENT REGARDING FEDERALLY SPONSORED RESEARCH DEVELOPMENT

N/A

REFERENCE TO A MICROFICHE APPENDIX

N/A

BACKGROUND OF THE INVENTION

The field of endeavor to which this invention pertains is the same as that of the use of real candles. In many instances where a real candle can be used, the present invention can be used instead, with little sacrifice of attractive ambiance, or authentic appearance. The benefit to be gained is that the present invention makes use of real candle wax to comprise the body of the device, and thus the attractiveness of candle wax, the authenticity, and the pleasant glow through qualities and differing dimensional features of real wax are not sacrificed in the creation of a safer alternative to a flame bearing candle. With all the attractive benefits, this electric candle does not use a real, and many more times dangerous, flame as the source of illumination. In addition, the flameless candle will last many times longer than a candle of equivalent size.

The prior art includes electronic candle simulators as those of Ignon (U.S. Pat. No. 5,097,180), Lederer (U.S. Pat. No. 6,017,139 and U.S. Pat. No. 6,066,924), Johnson (U.S. Pat. No. 4,510,556), Blackerby (U.S. Pat. No. 4,866,580), and St. Louis (RE37,168) which do not include the use of real candle wax or real pre-burn candle bodies as a foundational element for the creation of a simulated candle. In addition, while paying attention to the aspects of random flicker the above mentioned prior art, do not include development of aspects of flame movement, color and intensity matching in keeping with the realism of a real candle.

In prior art when real candle wax was used, such as that of Andeweg (U.S. Pat. No. 3,761,702) and Graff (U.S. Pat. No. 3,749,904), real wax was used, but the illumination came from within the candle. The invention of Adinamis (U.S. Pat. No. 2,532,800), uses real candle wax, but it is enclosed in a hollow cylindrical member, with varying amounts of accompanying ornamental and structural fixtural hardware that does not represent a stand alone candle. None of the prior art speaks of accurate volume-of-light output and color temperature matching or provides means for user adjustable rate of flicker.

BRIEF SUMMARY OF THE INVENTION

The present invention involves the use of real candle wax as a foundational element in the creation of a much safer electric replacement to a real flame candle.

The obstacle of lacking realism in the prior art is partially overcome because real wax is not substituted with an artificial medium. Real candle wax, including wax that is not doctored, or chemically altered in any way, is responsible for much of the inherent beauty of a traditional candle. Light, from a flame source, or an electric lamp, will not look the same when shining through an artificial medium, such as plastic, for example, as that which is shining through real wax. By adherence to a number of safety principles, the needed electronics of an electric candle can be used in conjunction with real wax, or previously used candles, to provide a 'candle' that is much safer to use. The resultant delicate nature of the present invention is not a deterrent as it is only as delicate as a real candle and the delicacy adds to the asthetic appeal of the candle.

The present invention also includes a flame shaped electric lamp assembly where proper attention is given to match to the size of it to a real flame. This assembly, connected with its circuit, and power supply option make possible simulated flame motion, and light color and intensity matching. These innovations are not touched upon heretofore in the prior art mentioned above. The resultant invention, is a much more realistic, less mechanical, candle simulation with accurate light color and intensity matching and 'flame' movement. The flame shaped assembly is formed with a medium that because of its irregular shape, and partial translucency, disguises the unnatural ahape and appearance of the lamps and wires embedded therein.

DETAILED DESCRIPTION OF THE INVENTION

Figure 1:
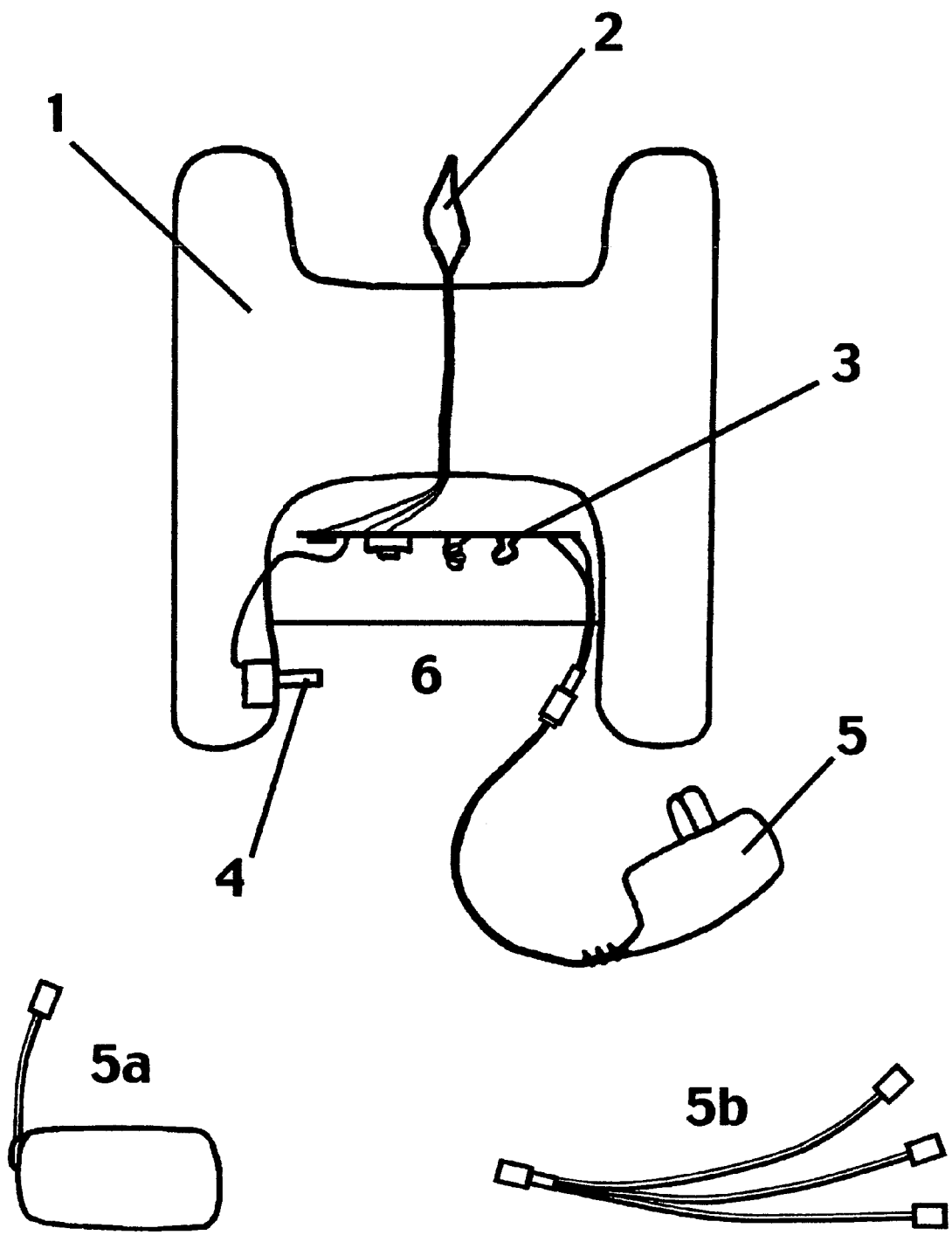
FIG. 1 shows a cutaway view of the flameless candle
Figure 2:
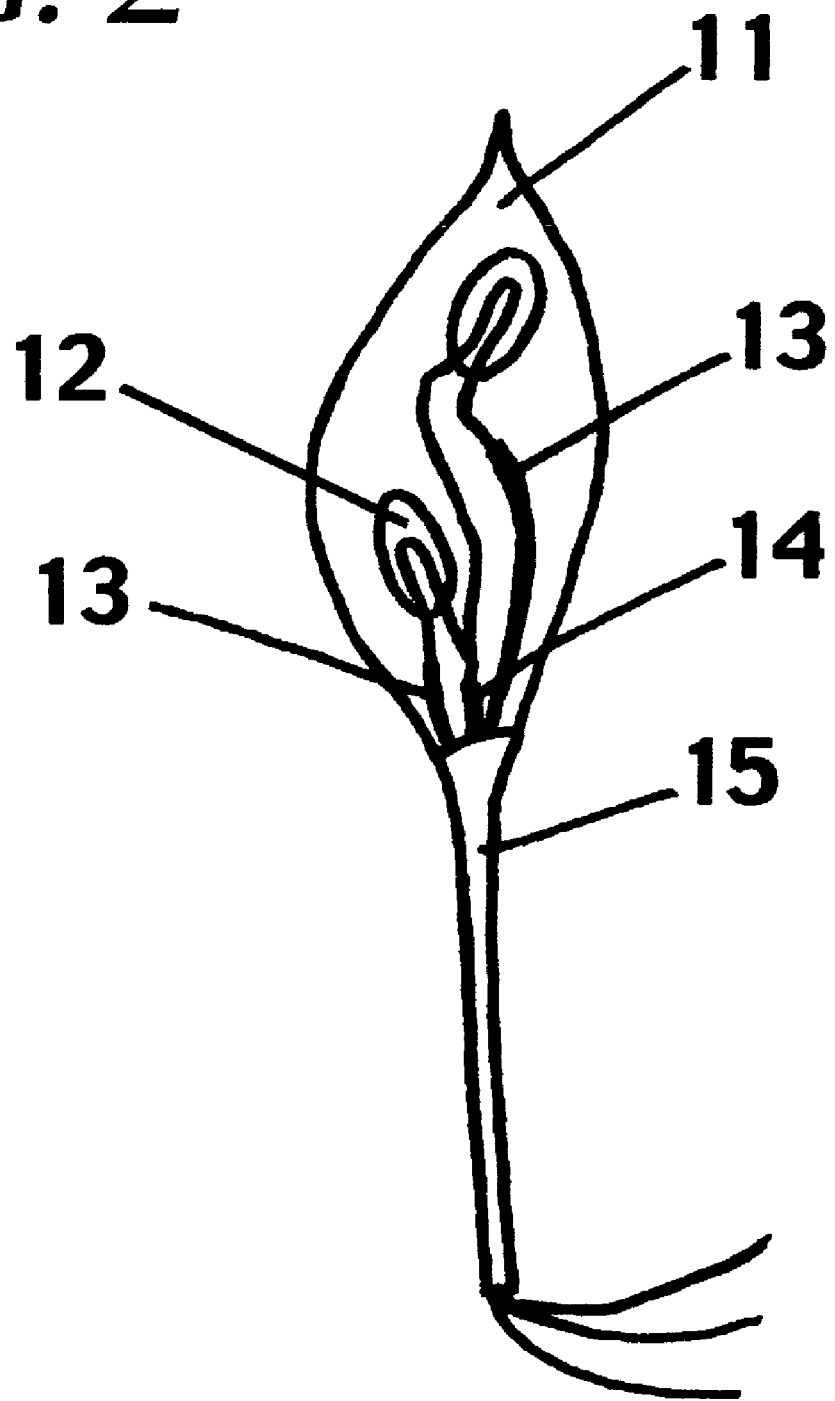
FIG. 2 shows a detail view of the flame/wick assembly
Figure 3:
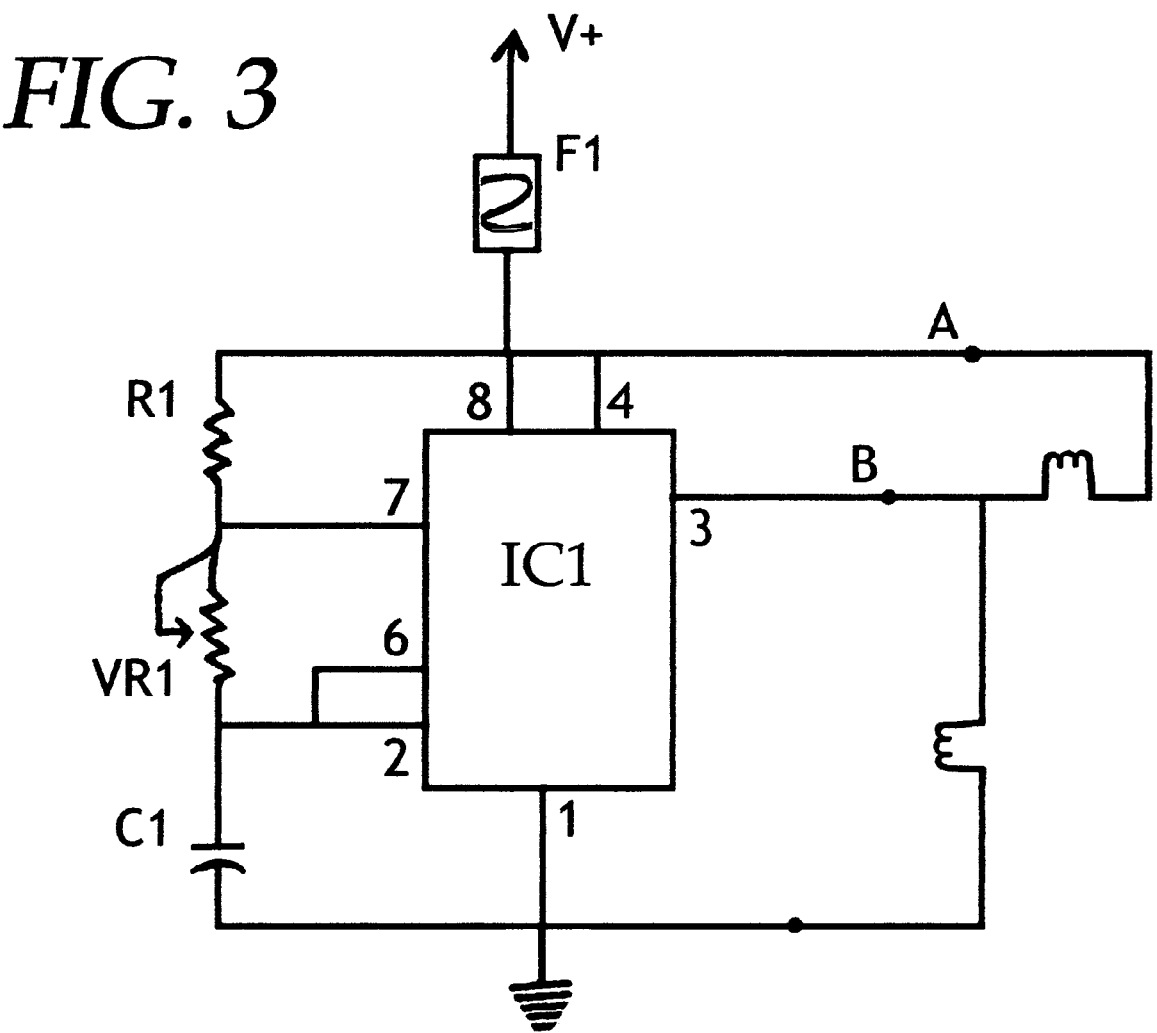
FIG. 3 shows an electrical schematic of the invention, with optional flame/wick variation
Figure 4:
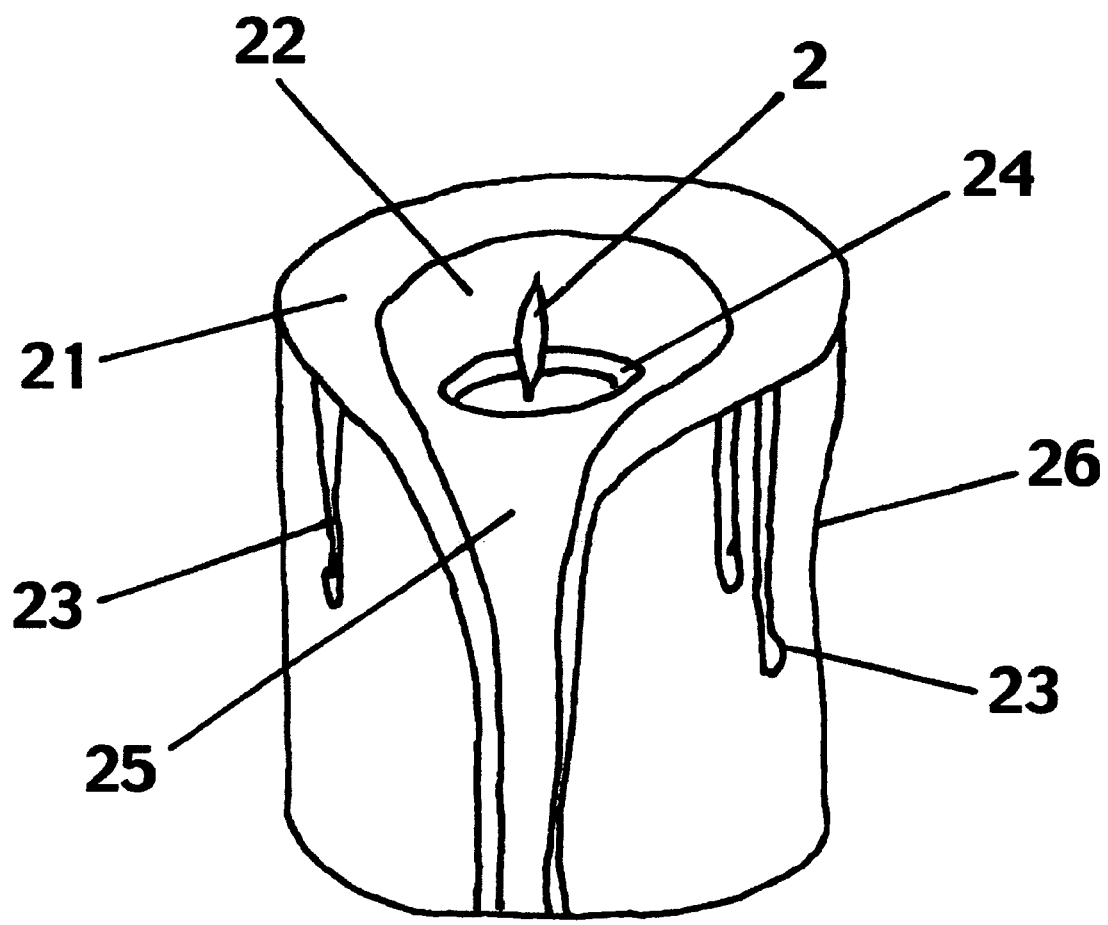
FIG. 4 shows a perspective view of the candle body with features

The flameless candle has its beginnings or its essence as a real candle. Real candle wax, or an actual pre-burnt, de-wicked, and hollowed out candle is used to form the body 1 of the flameless candle. In fact, there is no difference between the chemical composition of the flameless candle wax body 1 and a candle created for combustion. Therefore, all the richness and beauty of appearance, the glow-through qualities, the diversity of potential designs, including colors and essences, all remain intact.

The flameless candle is made of four parts.

The power supply 5 is a common configuration 12 volt 0.1 amp plug-in AC adapter providing dc voltage. This is connected to the electronic component 3 which is the next part.

The electronic portion 3 consists of a fuse, a 555 integrated circuit timer, a 47 k ohm resistor, a 0.22 mfd capacitor, a one meg ohm potentiometer, These are wired together to produce a variable oscillator circuit and then encased in resin, hot melt glue, or candle wax (or any combination of these). This part will be inserted and glued into the candle which is the next part.

The candle portion 1 is a typical, good quality, scented or unscented, store bought candle that has the bottom drilled out to accommodate the electronic portion 3. For appearance sake, the top portion of the candle is either burned or is made to appear burned with a torch, and/or a drill (to speed up the task of melting wax). All flameless candles have the flame/wick 2 portion situated below the height of some or all of the wall 21 of the recessed burn area 22. This is not only for attractive appearance, but also to protect the flame/wick 2 portion during packaging and shipping.

To look more real and interesting, flameless candles may have one or more of the following features created when the candle is formed.

Tempered candle drippings 23 are created when hot wax drips down the body of a candle and the droplets and streaks, after cooling, are gently reheated to reduce in size and for better adhesion to the candle body.

Burn rings 24 are created within the recessed burn area 22 by pools of wax heated significantly, and moments later drained, then reheated to produce an independent reduced level circular wax pool with a ring or rings defining the various burns. The appearance created mimics that of a candle that has been burnt two or more different times.

Spill crevices 25 are an area created when hot wax in a wax puddle breaches a wall 21 of the recessed burn area 22 and runs down the body of the candle, melting away the solid wax forming a runoff area (often in the shape of a 'V').

A heat warp 26 of the outer body is created by burning away wax to form a slightly concave area on one or more sides of the outside of the candle body. This makes it look as though the candle has been subject to long hours of candle flame heat and thus the body, or wall 21 of the recessed burn area 22, has warped or collapsed a little.

Once an attractive appearance is obtained, the wax is allowed to cool. A cavity is then drilled in the bottom of the candle 6 to hide the electronic portion 3, and a small hole (or holes, for a three wick candle) is drilled in the appropriate center or centers down through the top to prepare for the flameless wick portion 2.

The wick portion 2 is comprised of two 12 volt 60 milliamp micro lamps 12 with leads only. (no bases). These lamps are wired together thus. Two leads are twisted together 14, one from each light. A thin wire is attached to these two leads and two more wires are attached to each of the single remaining leads of the two lamps (thus three wires—the common is white and the other two wires are blue 13) A section of heat shrinkable tubing 15 is slid over three wires and pushed to the bases of the two lights The tubing is then heated to shrink in size and also grip around the wires. The light elements are then dipped in epoxy 11 a number of times and rolled and shaped, manipulated and cut, to form the shape of a flame. Part of the end of the heat shrink tubing 15 is also encased within the finished "flame" portion 2 of the wick for appearance sake and for structural support. This encased portion of the heat shrink tubing is black or marked the color of a burning wick.

The unit is assembled thus. A hole or holes for a three-wick candle is drilled at the appropriate or approximate center of the candle. The flame/wick portion is first tested, then inserted into this hole. Appropriate wick height is determined, for appearance, and glued fast with hot melt glue where the wired end of the "wick" pokes through into the electronics cavity 6 on the underside of the candle.

The electronics circuit 3, after being tested, is then positioned in the cavity 6 at the bottom of the candle so that the user-adjustable potentiometer 4 will be sufficiently recessed into the cavity 6 at a location that will provide convenient access. It is then glued in place, with the wiring thereof rising out of cavity, along with the wires of the flame/wick portion 2. The AC adapter 5, after polarity is checked, is then introduced and wiring connections are made between the flame/wick 2, the electronics bundle 3, and the AC adapter 5, (The connections are insulated). The wires are then stuffed into the available area of the electronics cavity 6 and hot melt glue, epoxy or candle wax are introduced to encapsulate all of it filling the cavity 6. Proper gluing strength is applied to the area around the AC adapter wire 5 so that its resultant exit from the cavity some strength. This is allowed to cool or set. The AC adapter 5, or a battery pack 5a may also be connected by means of a receptacle on the circuit board.

A flameless candle is an imitation of a real candle and has no flame. A flameless candle was designed to look like a real candle. For that reason, the color of the light was carefully mimicked by the flameless candle by measuring the voltage supplied to the subminiature assembly lamps 12 while the assembly was placed next to a real burning candle. This voltage was then adjusted to produce a good color match, and the voltage level recorded. This process was repeated many times to find an average that would account for any variances in individual lamps. The average was then the standard voltage that needed to be supplied to the lamps. This is important for realism because many candle simulators have a light color that is too white, or too orange, for example.

The same process was originally followed in the initial selection of the lamp for light output. A candle flame gives out a certain amount of light. This also needed to be matched. We found that at 12 volts, for example, that the light output was acceptably pleasing using a 60 ma lamp. Using two 60 ma lamps at 12 volts was an even better match. The resultant light output is within perhaps 30% range of that of a real candle, which we feel is an acceptable boundary. As in the above example, often the amount of light produced by candle simulators is far above or far below a real candle flame.

A flameless candle is designed to be safe. Basically, using small lights, a flameless candle is much safer than using a real flame candle. The circuitry inside is fused by a one-time protective fuse that protects the circuitry from overload when there is anything wrong and the circuitry overloads. The fuse is not replaceable. It is felt that the fuse is also sensitively fused so that the circuitry and candle will be protected well in the event that anything should go wrong. Basically the candle is a throw-away if anything goes wrong with it. It is made that way so there is that extra level of protection.

Flameless candles operate on electricity. Extra safety is involved because, flameless candles operate on 12 volts, thus low voltage. Thus the shock potential is limited to the UL approved AC adapter 5 only, as the candle body itself operates on 12 volts.

A flickering effect was also desired where the origin of the light would move similar to a real candle. It is an alternating flickering effect that uses two lights in the assembly 2 that imitate the realism of a real candle by providing an varying light source. The rate of flickering, supplied by the electronic circuit 3 is adjustable and has a setting of the rate that includes a constant-on capability. A different flickering action is also derived by switching two wires during the wiring of the flameless candle. By putting the common wire of the 'flame' portion, to the fused positive and connecting a 'flame' input wire to the output of the circuit board, a different lighting effect is created. This simple change of the flameless candle circuitry results in one light flickering and one light staying on. This may be a desired option because the volume of light created is more than that of the standard flameless flickering action, and more closely mimicking the amount of light produced by a real flame. While the lighting effect of standard flameless candle flickering action is dramatic and realistic, the lighting effect of a flameless candle wired in this (henceforth referred to as) alternative flicker wiring manner creates an effect that has an even more stunning likeness to a real candle in many applications. There is also a reduction in the brightness of the lamp that stays on all of the time when the flickering light is on. This is an added benefit in that it gives more flame action for the money, adding complexity to the glow, with no more components on the circuitboard. The effect has produced what many people have called a more tranquil effect, because there is less of a flashing effect, as one light always stays on and there is not that brief moment in the standard effect when the one light has just gone off, but the other has not yet come on. The alternative flicker wiring manner produces a candle that uses an extra 60% of electricity in producing this brighter, yet more calming effect.

The flameless candle is can also be wired to accommodate a battery as its power supply. This is accomplished by using a low power 555 timer IC instead of a standard 555 timer IC, and also using 5 volt pea lamps instead of 12 volt pea lamps. The power voltage is approx. 6 volts. The lamps draw 115 milliamps. The candle can run for approx. 18 hours on 4 AA batteries. One or two transistors, depending on which flicker pattern is used, are employed at the output of the timer to handle the extra current.

If the alternative flicker wiring manner is used, the candle will run for approx. 12 hours on 4 AA batteries. The battery pack 5a plugs in to the candle in the same spot as the AC adapter 5, or a ganging cord 5b (which would allow connection of more than one flameless candle to a power source). There is a space in the bottom of the candle 6 to accommodate and hide the battery pack 5a, or it can be located externally to the candle body. Rechargeable or regular batteries may be used.

The light intensity, when powered at optimum color match also matches the brightness of a real candle flame. It is important that neither element is overlooked of these two. Said lamps are encased in a clear or slightly yellow heat resistant transparent or translucent medium 11, one lamp being above and to the side of the other, formed in the same dimensions of a burning wick, so that the size and shape of the finished assembly 2 matches that of a real flame. The envelope, or encasing medium, is formed in a somewhat irregular shape, with uneven density so as to resemble the shape of a flame. This is so that the lamp will look less mechanical, and give of a less mechanical looking, more uneven light. A very slight natural yellowish tint can be added.

With a flameless candle you can have all the benefits of an active and interesting candle including essence, real wax and burnt look with no two candles the same. The candles never burn out essentially thus saving money. Nothing will replace a real candle of course, but this is something for instances when a real candle may not be practical, or safe, or otherwise desired. The light flickers and thus appears more similar to a real flame in instances than if the light was constant. These candles, are a lot safer than real candles, and it is the hopes that they can be manufactured to a standard that would allow them to be on continuously without being attended.

Also, in instances of remote location, where access is difficult, but placement is desired, these flameless candles can be wired directly into a switched circuit for convenience, such as in a high place like a ledge.

I claim:

1. A flameless candle comprising: a body portion, an electric flame portion, an electronic portion, and a power providing portion, wherein;

said body portion is made of real candle wax and formed in the shape of a real candle, a recessed burn area is provided in top portion of said body portion, said body portion has a hollowed out area underneath, said electric flame portion is comprised of one or more subminiature lamps disposed within a clear or slightly yellow transparent or translucent means for encasement, wherein said subminiature lamps are positioned substantially with one lamp above the other, said means for encasement having substantially the size and the shape of a candle flame, said electric flame portion is recessed below the top of the wall of said recessed burn area, said flame portion is disposed within said recessed burn area, volume of light emitted by said one or more subminiature lamps of said electric flame portion substantially equals that of a candle flame, said electronic portion is disposed within said hollowed out area of said body portion, said electronic portion has the ability to provide means for flickering of said one or more subminiature lamps, wherein a different flickering action is derived by switching of two wires during the wiring of said flameless candle, wherein said different flickering action results in one light flickering and one light staying on, wherein said different flickering action results in a reduction in the brightness of the lamp that stays on all of the time when the flickering light is on, wherein the rate of flickering supplied by said electronic portion is adjustable and wherein a setting of said rate includes a constant-on capability, said power providing portion comprises any one of the group of an AC adapter, a battery, and a rechargeable battery, said power providing portion provides a predetermined voltage to produce illumination of said one or more subminiature lamps to the color temperature of fire, said predetermined voltage is generally considered safe low voltage.

\* \* \* \* \*